United States Patent
Millet

(10) Patent No.: US 9,751,747 B2
(45) Date of Patent: Sep. 5, 2017

(54) PROCESS FOR DETECTING ANOMALIES DURING THE FILLING OF A LIQUID METERING DEVICE AND LIQUID METERING DEVICE

(75) Inventor: Frédéric Millet, Paris (FR)

(73) Assignee: GILSON SAS, Villiers le Bel (FR)

( * ) Notice: Subject to any disclaimer, the term of this patent is extended or adjusted under 35 U.S.C. 154(b) by 566 days.

(21) Appl. No.: 14/126,918

(22) PCT Filed: Jun. 14, 2012

(86) PCT No.: PCT/EP2012/061258
§ 371 (c)(1),
(2), (4) Date: Dec. 17, 2013

(87) PCT Pub. No.: WO2013/000716
PCT Pub. Date: Jan. 3, 2013

(65) Prior Publication Data
US 2014/0137980 A1    May 22, 2014

(30) Foreign Application Priority Data

Jun. 28, 2011 (FR) ...................... 11 55747

(51) Int. Cl.
*B67D 7/16* (2010.01)
*G01F 11/02* (2006.01)
(Continued)

(52) U.S. Cl.
CPC .............. *B67D 7/16* (2013.01); *B01L 3/0227* (2013.01); *G01F 11/023* (2013.01);
(Continued)

(58) Field of Classification Search
CPC B67D 7/16; B67D 7/18; G01F 11/023; G01F 11/029; G01F 23/14; G01F 25/00;
(Continued)

(56) References Cited

U.S. PATENT DOCUMENTS 6,022,747 A    2/2000  Gherson et al.
6,119,533 A *  9/2000  Gherson ............ G01N 33/4905
                                                702/32
(Continued)

FOREIGN PATENT DOCUMENTS

EP    0571100    11/1993
EP    2031403    3/2009
(Continued)

OTHER PUBLICATIONS

International Search Report and Written Opinion issued in PCT/EP2012/061258, Oct. 24, 2012.

*Primary Examiner* — Matthew G Marini
*Assistant Examiner* — Leo T Hinze
(74) *Attorney, Agent, or Firm* — Miles & Stockbridge P.C.

(57) ABSTRACT

Method for detecting anomalies during the filling of a liquid metering device with a liquid to be measured out, said metering device comprising at least one suction member and at least one pressure monitoring means arranged for measuring a pressure in relation to said suction member. The detection method comprises steps consisting of: performing a prior pressure calibration of the filling of the device, calculating for a desired volume a tolerance range having an upper limit and a lower limit on the basis of the prior pressure calibration and checking whether the pressure remains within the tolerance range during the filling of the metering device with the liquid to be measured out.

20 Claims, 9 Drawing Sheets

(51) Int. Cl.
*G01N 35/10* (2006.01)
*B01L 3/02* (2006.01)

(52) U.S. Cl.
CPC ....... *G01F 11/029* (2013.01); *B01L 2200/146* (2013.01); *B01L 2200/148* (2013.01); *G01N 35/1016* (2013.01)

(58) Field of Classification Search
CPC G01F 25/0092; G01N 35/10; G01N 35/1016; B01L 3/021; B01L 2200/146; B01L 2200/148
See application file for complete search history.

(56) References Cited

U.S. PATENT DOCUMENTS

| | | | |
|---|---|---|---|
| 6,938,504 B2 | 9/2005 | Camenisch | |
| 7,779,666 B2* | 8/2010 | Johansson | B01L 3/021 73/1.74 |
| 7,904,258 B2 | 3/2011 | Millet | |
| 7,917,313 B2* | 3/2011 | Ziegler | G01N 35/1016 702/100 |
| 7,964,160 B2* | 6/2011 | Zuppiger | B01L 3/021 422/500 |
| 8,874,399 B2* | 10/2014 | Beumer | G01N 35/1016 702/100 |
| 2007/0169571 A1* | 7/2007 | May | B01L 3/0217 73/864.13 |
| 2010/0132486 A1* | 6/2010 | Millet | B01L 3/0227 73/864.13 |

FOREIGN PATENT DOCUMENTS

| | | |
|---|---|---|
| EP | 2302397 | 3/2011 |
| FR | 2927999 | 9/2010 |
| JP | 6-501558 A | 2/1994 |
| JP | 10-048220 A | 2/1998 |
| WO | WO 2006/040386 | 4/2006 |

* cited by examiner

PROCESS FOR DETECTING ANOMALIES DURING THE FILLING OF A LIQUID METERING DEVICE AND LIQUID METERING DEVICE

CROSS-REFERENCE TO RELATED APPLICATIONS

This application is a National Stage Entry under 35 U.S.C.§371 of International Application No. PCT/EP2012/061258, filed Jun. 14, 2012, which claims the benefit of FR Patent Application No. 1155747, filed Jun. 28, 2011, the contents of which are herein incorporated by reference.

FIELD OF THE INVENTION

The invention relates to the field of precision liquid metering.

In the fields of medicine, pharmacology and chemistry, it is not unusual to need precise and reproducible metering of a liquid to be measured out.

Indeed, this precision will determine the correct stoichiometry of the final solution, and thus the efficacy thereof, the correct values of a chemical or physiological analysis and, in the field of pharmacology, the efficacy and safety of a medicinal product preparation.

At the present time, this precision is generally achieved using an automated metering device. In some cases, for which the precision needs to be verifiable and/or guaranteed, these metering devices may use a system for detecting anomalies during the filling of the liquid metering device with the liquid to be measured out.

The invention relates more specifically to a method for detecting anomalies during the filling of a liquid metering device with a liquid to be measured out and to a liquid metering device using such a method.

STATE OF THE RELATED ART

Automated metering devices, such as automated pipettes or automated chemical analysers, are generally metering devices comprising at least one suction member, also known as a cone, intended to contain liquid to be measured out, automated filling means suitable for filling the suction member in an automated manner. These automated metering devices may also comprise a pressure sensor, arranged for measuring the pressure in the filling means or in the cone, and a processing system arranged for controlling the automated filling means and monitoring the pressure measured by the pressure sensor.

In recent years, with the generalisation of automated liquid metering devices, in parallel with the increased need for precision and reproducibility in metering, methods for detecting anomalies during filling has been implemented.

European patent application EP 0571100 A describes such a method for detecting anomalies. This method consists, prior to metering the liquid to be measured out to a desired volume, recording a reference pressure curve at the same volume. In this way, during the filling of the metering device with the desired volume of a liquid to be measured out, the processing system is suitable for comparing the pressure curve measured with the reference pressure curve. Any significant deviation gives rise, following the implementation of such a method, to the detection by the processing system of an anomaly during the filling of the metering device.

While such a method is suitable for detecting an anomaly for a desired volume of liquid to be measured out, this method requires, during the implementation thereof, prior pressure calibration to said desired volume. In this way, a metering device using such a method can only be suitable for detecting anomalies at a low number of volumes of liquid to be measured out, any non-pre-calibrated volume requiring a prior pressure calibration operation.

Similarly, the method for detecting anomalies described in the patent U.S. Pat. No. 6,938,504 B is similar to that of the patent application EP 0571100 A, this detection method comprising an additional step for calculating a tolerance range so as to limit the risk of "false positives", i.e. detecting anomalies which do not exist. It is this also necessary, when implementing this method, to envisage a prior pressure calibration of the metering device to the desired volume.

In this way, a metering device implementing such a method may only be suitable for detecting anomalies with a low number of volumes of liquid to be measured out, any non-pre-calibrated volume requiring a prior pressure calibration operation.

The patent application EP 2302397 A describes a method for detecting anomalies based on a continuous record of the pressure variation using the pressure sensor during the filling of the suction member and an extrapolation of the pressure value on the basis of the pressure variation measurements recorded. In this way, with such a method, the limits of a pressure tolerance range are calculated at each time based on both the latest pressure value measured by the pressure sensor and the instantaneous pressure variation measured, the deviation of the measured pressure from this tolerance range being interpreted as an anomaly in respect of the filling of the metering device.

Such a method is thus suitable for detecting anomalies regardless of the desired volume of liquid to be measured out without requiring prior pressure calibration of the metering device to said volume. Nevertheless, such a method has the disadvantage of only functioning during the vacuum increasing phase corresponding to the actuation of the filling means, this method not being operational in the following vacuum relaxation phase, or relaxation phase. Furthermore, such a method is not suitable for detecting a gradual shift in the pressure variation curve which may originate from, for example, an insufficient filling means speed.

DESCRIPTION OF THE INVENTION

The present invention is intended to remedy these drawbacks.

One of the aims of the invention is thus that of providing a method for detecting anomalies during the filling of liquid metering device with a liquid to be measured out, said method being suitable for detecting anomalies during the filling of a liquid metering device with any volume of liquid to be measured out without requiring further prior pressure calibration with said any volume of liquid to be measured out, the method being active at least during the relaxation phase following the vacuum increasing phase corresponding to the actuation of the filling means.

A further aim of the invention is that of providing a method for detecting anomalies during the filling of a liquid metering device with a liquid to be measured out, said method being suitable for detecting anomalies with a large number of volumes of liquid to be measured out with a low number of prior pressure calibration steps, the method being active at least during the relaxation phase following the vacuum increasing phase corresponding to the actuation of the filling means.

For this purpose, the invention relates to a method for detecting anomalies during the filling of a liquid metering device with a liquid to be measured out, said device comprising:
- at least one suction member intended to be in contact with the liquid to be measured out and to contain same during the filling of the metering device,
- at least one filling means arranged for filling, in an automated manner, the suction member, said filling means comprising at least one zone communicating with the suction member, said zone containing a gas,
- and at least one pressure monitoring means arranged for measuring the pressure in the zone of the filling means or in a zone of the suction member containing a gas, the detection method comprising steps consisting of:
a) performing a prior pressure calibration of the filling of the metering device, this pressure calibration being carried out with at least two reference volumes so as to define a reference filling curve for each of the at least two reference volumes,
b) defining a desired volume of liquid to be measured out,
c) calculating for the desired volume a tolerance range having an upper limit and a lower limit, the upper and lower limits of the tolerance range being calculated on the basis of the reference filling curves,
d) filling the suction member with the liquid to be measured out for a time dt,
e) measuring the pressure using the pressure monitoring means,
f) checking whether the pressure is within the tolerance range and if the pressure is in the tolerance range returning to step d) until a filling time corresponding to the desired volume of liquid to be measured out is attained,
g) if the pressure is outside the tolerance range, reporting that an anomaly has been detected.

Such a method is suitable, with pressure calibration with a low number of reference volumes, optionally equal to two, for detecting an anomaly at any volume of liquid to be measured out.

In this method, step d) and step e) may also equally well be successive, simultaneous or reversed.

The method may further comprise a step h) consisting of calculating, on the basis of the pressures measured during the filling of the metering device, the volume of liquid to be measured out in the suction member and a step i) consisting of, if the difference between the desired volume and the calculated volume of liquid to be measured out is greater, in absolute terms, than a threshold value, reporting that an anomaly has been detected.

Such steps enable an additional check that the metering device has been filled correctly and thus that the liquid to be measured out has been measured out correctly.

Step c) may comprise a step c') consisting of calculating a filling curve calculated for the desired volume on the basis of the reference filling curves, and a step c'') during which the calculation of the upper and lower limits of the tolerance range comprises a calculation step consisting for the upper limit and the lower limit of respectively subtracting and adding a pressure value ΔP to the calculated filling curve.

The term calculating on the basis of the reference filling curves denotes equally well calculating on the basis of the reference filling curves per se, calculating on the basis of characteristic values of these references filling curves or calculating both on the basis of the reference filling curves and on some of the characteristic values thereof.

Such steps c') and c'') are suitable for calculating an optimised tolerance range for the desired volume of liquid to be measured out, this tolerance range being calculated on the basis of both a filling curve calculated for said desired volume and a tolerance pressure value ΔP.

Step c) may comprise a step c') consisting of calculating a calculated filling curve for the given volume on the basis of the reference filling curves, and a step c''') during which the calculation of the upper and lower limits of the tolerance range comprises a calculation step consisting, for the upper limit and the lower limit, of respectively creating a positive and negative time lag by a time value Δt.

Such steps c') and c''') are suitable for obtaining an optimised tolerance range for the desired volume of liquid to be measured out, this tolerance range being calculated on the basis of both a filling curve calculated for said desired volume and a time lag of a time value Δt.

Step a) may comprise a step a') consisting of recording pressure values measured using the pressure monitoring means during the filling of the suction member with a reference volume of liquid and a step a'') consisting of determining the filling curve corresponding to the pressure curve obtained in step a'), this step a'') also optionally consisting of determining the characteristic values corresponding to said pressure curve, steps a') and a'') being carried out for each of the reference volumes.

Such steps are suitable for determining characteristic values for each of the reference volumes thus facilitating the processing of the reference curves for the tolerance range calculation.

The characteristic values of the pressure curve determined during step a'') may comprise at least one characteristic value selected in the group comprising:
- a maximum vacuum pressure value $P_{max}$ corresponding to the maximum vacuum pressure value reached during filling,
- a maximum vacuum pressure time $t_{max}$ corresponding to the time at which the maximum pressure vacuum is reached,
- a residual vacuum pressure $P_a$, corresponding to the residual vacuum pressure after filling the metering device,
- and a characteristic time τ representing the rate of decline of the vacuum pressure after the vacuum pressure $P_{max}$ has been reached.

Such characteristic values are suitable for optimal characterisation of the pressure variation curves for each of the reference volumes. These values may also be suitable, when calculated for a desired volume of liquid to be measured out, for determining a theoretical filling curve for said desired volume of liquid to be measured out.

Step c') may comprise a step consisting of linearly interpolating the filling curve and/or characteristic values of the filling curve at the desired volume on the basis of at least two reference volume filling curves and/or characteristic values of the pressure curves of at least two reference volumes.

Such a filling curve at the desired volume and/or such characteristic values of the filling curve at the desired volume are suitable for calculating a filling curve at said volume, suitable for defining and/or obtaining a filling curve calculated on the basis of the reference filling curves and/or characteristic values of said curves substantially approximating a filling curve which could be obtained on the basis of a reference curve at the desired volume.

According to a first embodiment of the method, during steps c'') and c'''), the upper and lower limits of the tolerance range are calculated on the basis of the calculated filling curve using the following formulae:

$$P_+(t) = P_{ref}(t) + \Delta P + \left|\frac{dP(t)}{dt}\right| \times \Delta t,$$

$$P_-(t) = P_{ref}(t) - \Delta P - \left|\frac{dP(t)}{dt}\right| \times \Delta t,$$

where $P_+(t)$ and $P_-(t)$ are the upper and lower limits of the tolerance range at the time t, $P_{ref}(t)$ is the pressure calculated at the time t on the basis of the calculated filling curve and P(t) is the pressure variation measured at the time t.

According to one option of the invention, $$\left|\frac{dP(t)}{dt}\right|$$

may be calculated in step c''') by calculating the variation of P(t) between the time t-dt and the time t using the following formula:

$$\left|\frac{dP(t)}{dt}\right| = \left|\frac{P(t) - P(t-dt)}{dt}\right|.$$

According to a further option of the invention, during steps c'') and c'''), the upper and lower limits of the tolerance range may be calculated on the basis of the calculated filling curve using the following formulae:

$$P_+(t) = P_{ref}(t) + \Delta P + \left|\frac{dP_{ref}(t)}{dt}\right| \times \Delta t,$$

$$P_-(t) = P_{ref}(t) + \Delta P - \left|\frac{dP_{ref}(t)}{dt}\right| \times \Delta t,$$

where $P_+(t)$ and $P_-(t)$ are the upper and lower limits of the tolerance range at the time t, $P_{ref}(t)$ is the pressure calculated at the time t on the basis of the calculated filling curve.

Such formulae, for calculating the upper limit and lower limit, are suitable for defining the limits of the tolerance range accounting for both a tolerance on a phase lead or lag of the filling means and a tolerance on pressure measurement errors.

According to one alternative embodiment of the invention, the method further comprises, between steps c) and d), a step c*) consisting of operating the filling means for the time $t_{max}$ calculated for the desired volume.

Such a filling time is suitable for obtaining the actuation of the filling device required to fill the metering device to the desired liquid volume.

According to a further embodiment of the method, the reference and calculated filling curves may be the pressure variation curves after the corresponding time $t_{max}$.

Such filling curves are suitable for detecting errors during the filling of the metering device over the filling period following the actuation of the filling means.

According to a further embodiment of the method, the reference and calculated filling curves are the variation curves of the factor $P_{cor}$ after the time $t_{max}$, the factor $P_{cor}(t)$ being equal to $$\frac{P(t) - P_a}{P_{max} - P_a}.$$

Such a factor $P_{cor}$ is suitable for obtaining reference curves having, for the period following the actuation of the filling means, the same value at the time origin, the measured pressure being divided by the characteristic vacuum pressure value $P_{max}$, and the same limit after complete filling of the metering device, the residual vacuum pressure being subtracted both from the measured vacuum pressure on the numerator and the pressure $P_{max}$ on the denominator.

According to a further embodiment of the method, the reference and calculated filling curves may be the variation curves of the factor $P'_{cor}$ after the time $t_{max}$ as a function of a time variable $t_{cor}$, the factor $P'_{cor}(t_{cor})$ being equal to $$\frac{P(t_{cor}) - P_a}{P_{max} - P_a}$$

and the time variable $t_{cor}$ cor being equal to $$\frac{t - t_{max}}{\sqrt{P_{max} - P_a}}.$$

Such a factor $P'_{cor}$ and such a time variable $t_{cor}$ are suitable for obtaining similar filling curves whether for the reference filling curves or the calculated filling curve. The slight variations therebetween enable superior precision in respect of the determination of the calculated filling curve.

According to a further embodiment of the method, the reference and calculated filling curves are the variation curves of the factor $P''_{cor}$ after the time $t_{max}$ as a function of a time variable $t_{cor}$, the factor $P''_{cor}(t_{cor})$ being equal to $$\sqrt{\frac{P(t_{cor}) - P_a}{P_{max} - P_a}}$$

and the time variable $t_{cor}$ being equal to $$\frac{t - t_{max}}{\sqrt{P_{max} - P_a}}.$$

Such a factor $P''_{cor}$ and such a time variable $t_{cor}$ are suitable for providing filling curves having an approximately linear variation thus limiting the number of measurements for determining whether filling has been carried out correctly, each filling curve having an origin value of 1, it may be considered that a single measurement is necessary to check whether the entire filling of the metering device has been carried out correctly.

The invention also relates to a liquid metering device suitable for implementing a method according to the invention, the device comprising:
    at least one suction member intended to be in contact with the liquid to be measured out and to contain same during the filling of the metering device,
    at least one filling means arranged for filling, in an automated manner, the suction member, said filling means comprising at least one zone communicating with the suction member, said zone containing a gas, at least one pressure monitoring means arranged for recording the pressure in the zone of the filling means or in a zone of the suction member containing a gas, warning means suitable for reporting the presence of an anomaly control and calculating means arranged for controlling the filling means and at least one pressure monitoring means, the control and calculating means being suitable for carrying out a pressure calibration of the filling of the metering device with at least two reference volumes and defining a reference curve for each of the at least two volumes, for calculating the upper and lower limits of the tolerance range for the desired volume on the basis of the reference curves and for checking whether the pressure remains in said tolerance range during filling, said control and calculating means being further arranged for communicating with the warning means.

Such a device is suitable for providing qualified metering of a liquid since the filling step with said liquid to be measured out may be monitored using a method for detecting anomalies.

The metering device may also implement a method for detecting anomalies on the release of the liquid to be measured out.

Such a device makes it possible to ensure that all the liquid contained in the suction member is released, this release being monitored using a method for detecting anomalies on the release of the liquid to be measured out.

BRIEF DESCRIPTION OF THE FIGURES

The present invention will be understood more clearly on reading the description of examples of embodiments, given merely for indicative and non-limiting purposes, with reference to the appended figures wherein.

The various parts shown in the figures are not necessarily represented in a uniform scale, so as to increase the legibility of the figures.

By convention, in the set of graphs shown in FIGS. 2, 5, 6, 7 and 12, the curves represent pressure variations illustrating the vacuum pressure present in the suction chamber of the filling means, a positive value is thus equivalent to a vacuum in the suction chamber and a negative value to an overpressure, the origin of the pressures corresponding to atmospheric pressure.

DETAILED DESCRIPTION OF PARTICULAR EMBODIMENTS

Figure 1:
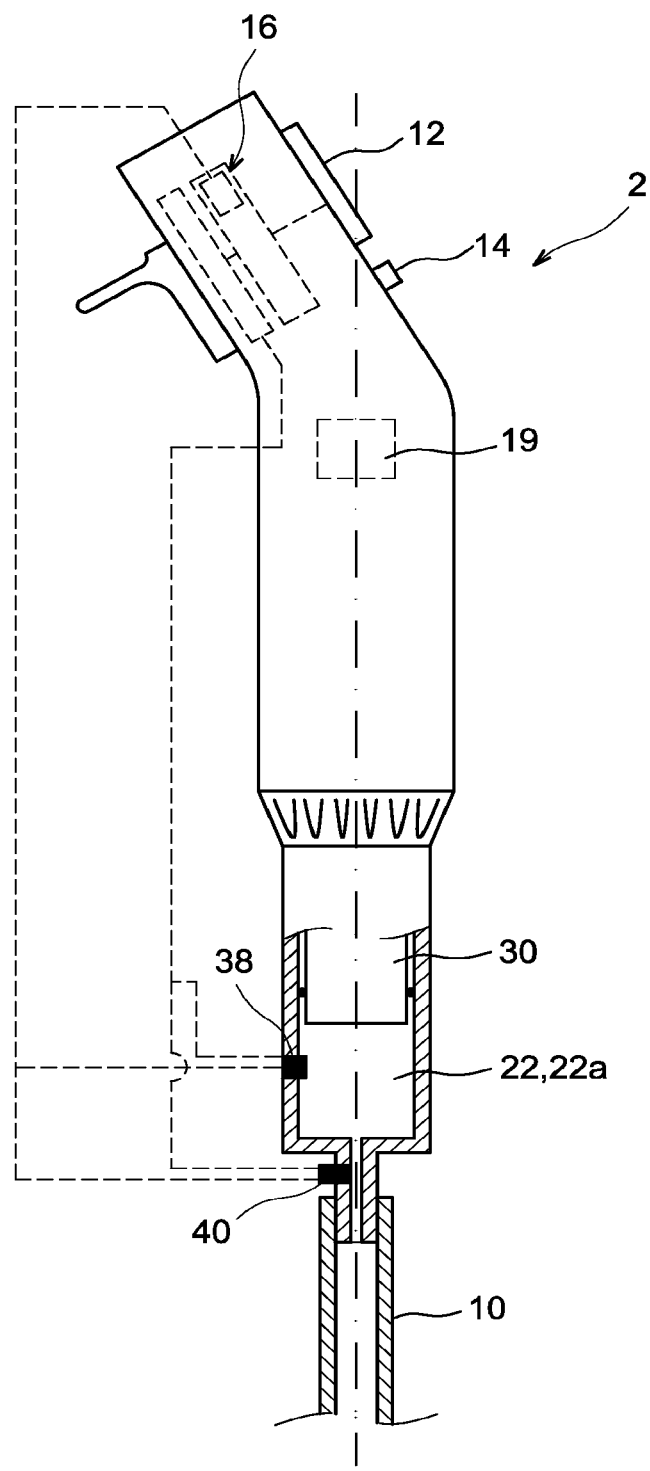
FIG. 1 illustrates an example of a liquid metering device suitable for implementing a method for detecting anomalies according to the invention.

FIG. 1 illustrates an automated pipette 2 suitable for implementing a method for detecting anomalies during the filling of the pipette 2 with a liquid to be measured out.

Such a pipette 2 comprises:

a suction chamber 22 having a gas zone 22a, a suction cone 10 communicating with the suction chamber 22 and acting as a suction member, said suction cone 10 being intended to contain the liquid to be measured out and generally being a disposable detachable suction cone 10, a motorised plunger 30 in the suction chamber 22 suitable for filling the suction cone 10 with the liquid to be measured out, this plunger 30 acting as automated filling means with the suction chamber 22, a pressure sensor 38 arranged for recording the pressure in the gas zone 22a and acting as pressure monitoring means, a screen 12 acting as warning means, a processing system 16 communicating with the pressure sensor 38 and suitable for controlling the motor 19 actuating the plunger 30 and the display of the screen 12, said system acting as control and calculating means.

Such a pipette 2 being similar, apart from the programming of the processing system, to a pipette 2 implementing a viscosity measurement, a full description is available in the document FR 2927999, the references in FIG. 1 being identical to those in said document so as facilitate the transition from the present description to the document FR 2927999.

It should also be noted that while the pipette 2 illustrated in FIG. 1 has a second pressure sensor 40 on the suction cone 10 for measuring the atmospheric pressure, the second pressure sensor 40 is not necessary for the invention and is present in the sole aim of also enabling a measurement of the viscosity of the liquid to be measured out.

With such a pipette 2, during the filling of the suction cone 10 with a volume of liquid to be measured out, the pressure sensor 38 will be suitable for monitoring the pressure values in the gas zone 22a.

Figure 2:
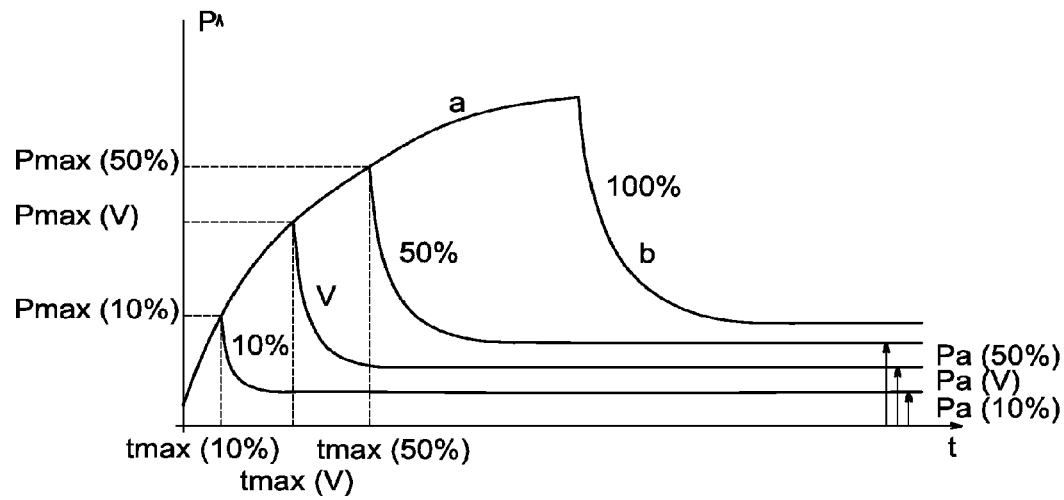
FIG. 2 illustrates pressure variation curves at various volumes of a metering device.

FIG. 2 illustrates pressure variation curves as a function of time obtained for various volumes of liquid to be measured out. The volumes of liquid to be measured out, apart from the volume V illustrating the possible operating mode of the pipette for any volume of liquid to be measured out, are expressed as a percentage of the nominal capacity of the pipette 2. In this way, in FIG. 2, the liquid volumes shown are 10%, 50% and 100% of the nominal capacity of the pipette 2.

It can be seen in these curves that the pressure variation has, for each of the aforementioned volumes, a similar pressure variation with two different filling phases:

a first vacuum increasing phase a) corresponding to the actuation of the plunger 30 and a second vacuum relaxation phase b) corresponding to the suction of the liquid to be measured out after the end of the actuation of the plunger 30.

FIG. 2 shows that, during the first phase, the pressure variation is substantially identical for each of the volumes, the difference being the maximum vacuum pressure value $P_{max}$ and the time $t_{max}$ at which this maximum vacuum pressure value $P_{max}$ is reached.

These two values, $P_{max}$ and $t_{max}$, are thus characteristic values, for this first phase, of the volume of liquid to be measured out.

The second phase, corresponding to the relaxation of the vacuum, as illustrated in FIG. 2, is a phase during which, after the end of the actuation of the plunger 30, the liquid continues to be aspirated until a residual vacuum pressure $P_a$ is reached. This residual vacuum pressure $P_a$, varying with the volume of liquid to be measured out, is a characteristic value of the volume of liquid to be measured out.

The value $P_a$ is generally measured by measuring the pressure variation in the suction chamber 22 during the filling of the pipette 2 at a given volume and by defining a baseline pressure value from which the vacuum pressure value reached is $P_a$. This threshold may be, for example, 1 mbar/s.

During this second phase, the pressure relaxation rate may be characterised by a characteristic time which may be called τ. This characteristic time τ may be determined with the following formula:

$$\tau = \frac{t - t_{max}}{1 - \sqrt{\left(\frac{P(t) - P_a}{P_{max} - P_a}\right)}}$$

This calculation may be made at any time during the pressure relaxation phase. In this way, to ensure satisfactory precision, this characteristic time may be calculated using a mean at a plurality of different times t during the vacuum relaxation phase.

In this way, on the basis of these various parameters $P_{max}$, $t_{max}$, $P_a$ and τ, it is possible to calculate the theoretical pressure variation curve corresponding to the second phase, for a given liquid volume. This equation is as follows:

$$P_{ref}(t) = [P_{max} - P_a] \times \left(1 - \frac{t - t_{max}}{\tau}\right)^2 + P_a \quad (1)$$

The pressure variation during the first filling phase being substantially identical regardless of the volume of liquid to be measured out, the theoretical pressure variation curve during the second phase being suitable for being known and the time to change from one phase to the other being also suitable for being known, the knowledge of the various characteristic parameters at a given volume thus makes it possible to reproduce a pressure curve corresponding to said given volume.

It is possible to determine with sufficient precision the characteristic values for a given volume by performing a linear extrapolation on the basis of the characteristic values at the reference volumes.

In this way, the characteristic values $P_{max}$, $t_{max}$ and $P_a$ for a volume V may be determined according to this procedure and with the following equations:

$$P_{max} = P_{max\_V2} \frac{V - V_1}{V_2 - V_1} - P_{max\_V1} \frac{V - V_2}{V_2 - V_1}, \quad (2)$$

$$t_{max} = t_{max\_V2} \frac{V - V_1}{V_2 - V_1} - t_{max\_V1} \frac{V - V_2}{V_2 - V_1}, \quad (3)$$

$$P_a = P_{a\_V2} \frac{V - V_1}{V_2 - V_1} - P_{a\_V1} \frac{V - V_2}{V_2 - V_1}, \quad (4)$$

where $V_1$ and $V_2$ are the reference volumes for which the characteristic values are known, $P_{max\_V1}$ and $P_{max\_V2}$ are the maximum vacuum pressures of $V_1$ and $V_2$, respectively, $t_{max\_V1}$ and $t_{max\_V2}$ are the times $t_{max}$ at which the maximum vacuum pressure values are reached for $V_1$ and $V_2$, respectively, and $P_{a\_V1}$ and $P_{a\_V2}$ are the residual vacuum pressures of $V_1$ and $V_2$, respectively.

These values $V_1$ and $V_2$ are, for these equations, and for all the subsequent equations using same, preferentially chosen so as to encompass the desired volume value, i.e. V, V1 and V2 observe the following inequation:

$$V_1 < V < V_2$$

If a plurality of reference volumes, for which the characteristic values are known, are accessible, the volumes $V_1$ and $V_2$ are preferentially chosen as the reference volume directly lower than the liquid volume V and the directly higher reference volume, respectively. For example, in the case illustrated in FIG. 2, the volume $V_1$ corresponds to 10% of the nominal capacity of the pipette 2 and the volume $V_2$ corresponds to 50% of the nominal capacity of the pipette 2.

For the characteristic time τ, a mere linear extrapolation is not suitable for obtaining sufficient precision, it is necessary to use a more complex equation which is as follows:

$$\tau = \frac{\sqrt{P_{max} - P_a}}{V_2 - V_1} \left( \frac{\tau_{V2}(V - V_1)}{\sqrt{P_{max\_V2} - P_{a\_V2}}} - \frac{\tau_{V1}(V - V_2)}{\sqrt{P_{max\_V1} - P_{a\_V1}}} \right) \quad (5)$$

where $\tau_{V1}$ and $\tau_{V1}$ are the characteristic times of $V_1$ and $V_2$, respectively.

These various equations are thus suitable, on the basis of characteristic values of two reference volumes of the automated pipette 2, for calculating the characteristic values, and thus obtaining the theoretical pressure variation for the filling of the automated pipette 2, regardless of the desired volume of liquid to be measured out.

On the basis of the pressure curves, it is also possible to determine the characteristic value S which is characteristic of the ratio between the volume of liquid contained in the suction cone 10 after filling and the integral of the root of the pressure variation during the filling of the pipette 2.

This characteristic value may be calculated using the following equation:

$$S(V) = \frac{\sqrt{\frac{\rho}{2}} V}{\int_0^{t\,max} \sqrt{P(t)}\, dt + \int_{t\,max}^{t\,max+\tau} \sqrt{P(t) - P_a}\, dt}$$

where $\rho$ is the viscosity of the liquid.

This parameter may thus be suitable, for a given volume of liquid to be measured out, for checking that the pressure variation during the filling of the pipette 2 is consistent with the given volume to be measured out, and thus checking whether the volume of liquid to be measured out contained in the suction cone 10 is indeed that expected.

Indeed, according to the above equation, the volume of liquid filling the suction cone 10 after filling is equal to:

$$V_{cal} = S \sqrt{\frac{2}{\rho}} \left( \int_0^{t\,max} \sqrt{P(t)}\, dt + \int_{t\,max}^{t\,max+\tau} \sqrt{P(t) - P_a}\, dt \right)$$

This volume $V_{cal}$ may easily be compared to the volume of liquid to be measured out.

Similarly, for the characteristic values $P_{max}$, $t_{max}$ and $P_a$, it is possible to determine the value of S at a given volume by making a linear extrapolation according to the following equation:

$$S = S_{V2} \frac{V - V_1}{V_2 - V_1} - S_{V1} \frac{V - V_2}{V_2 - V_1} \quad (6)$$

where $S_{V1}$ and $S_{V2}$ are the characteristic values S for the reference volume $V_1$ and for the reference volume $V_2$, respectively.

In this way, all or some of the characteristic values $P_{max}$, $t_{max}$, $P_a$, $\tau$ and S may be calculated for any volume of liquid to be measured out and be used to detect an anomaly during the filling of the pipette 2 with said volume of liquid to be measured out.

The processing system 16 of the pipette 2 is suitable for implementing this principle on implementing a method for detecting an anomaly during the filling of the pipette 2.

Figure 3:
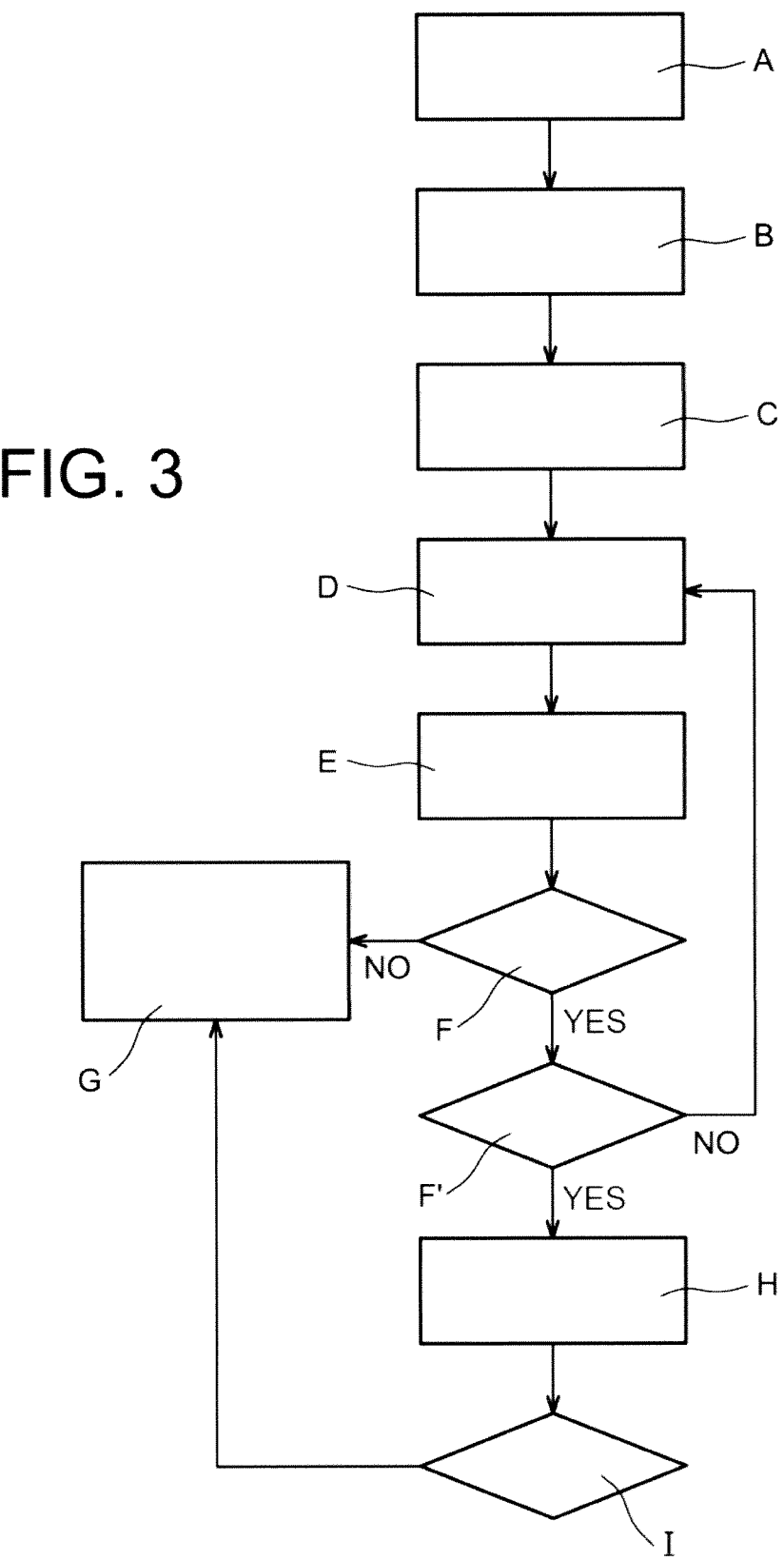
FIG. 3 is a simplified flow chart explaining the various steps for implementing a method for detecting anomalies during the filling of a liquid metering device with a liquid to be measured out.

FIG. 3 is a flow chart showing the main steps of such a method. Such a method comprises steps consisting of:

A) performing a prior pressure calibration of the filling of the pipette 2, this prior pressure calibration being performed with at least two reference volumes so as to determine a filling curve and at least some of the characteristic values $P_{max}$, $t_{max}$, $P_a$, $\tau$ and S for each of these at least two volumes, B) defining a desired volume of liquid to be measured out by the user, C) calculating for the desired volume a tolerance range having an upper limit and a lower limit, the upper and lower limits of the tolerance range being calculated using characteristic values and/or for reference volumes obtained in step A), D) filling the suction code 10 with the liquid to be measured out for a time dt, E) measuring the pressure using the pressure sensor 38 of the air zone 22a, F) checking whether the pressure is within the tolerance range, F') checking whether t is greater than or equal to the filling time corresponding to the desired volume, G) reporting on the screen 12 that an anomaly has been detected, H) calculating the volume of liquid to be measured out contained in the suction cone, I) checking whether the difference between the calculated volume of liquid to be measured out and the desired volume is greater in absolute terms than a threshold value.

In a first embodiment of the pipette 2, the processing system 16 is suitable for processing filling curves corresponding to pressure variation curves during the filling of the pipette 2.

According to this embodiment, the pressure calibration step A) is suitable, for at least two reference volumes, for determining the reference pressure variation curves, these curves acting as filling curves. During this step, one of the reference volumes is preferentially the volume corresponding to the nominal capacity of the pipette 2.

During this step, the processing system methodes the reference filling curves in order to determine for each of the reference volumes characteristic values $P_{max}$, $t_{max}$, $P_a$, $\tau$ and S at these reference volumes.

Once these characteristic values have been recorded, the pipette 2 may be used with any volume of liquid to be measured out. Indeed, equations (2), (3), (4), (5) and (6), are suitable, on the basis of the characteristic values of the reference volumes, for extrapolating the corresponding characteristic values regardless of the liquid volume to be measured out.

Figure 4:
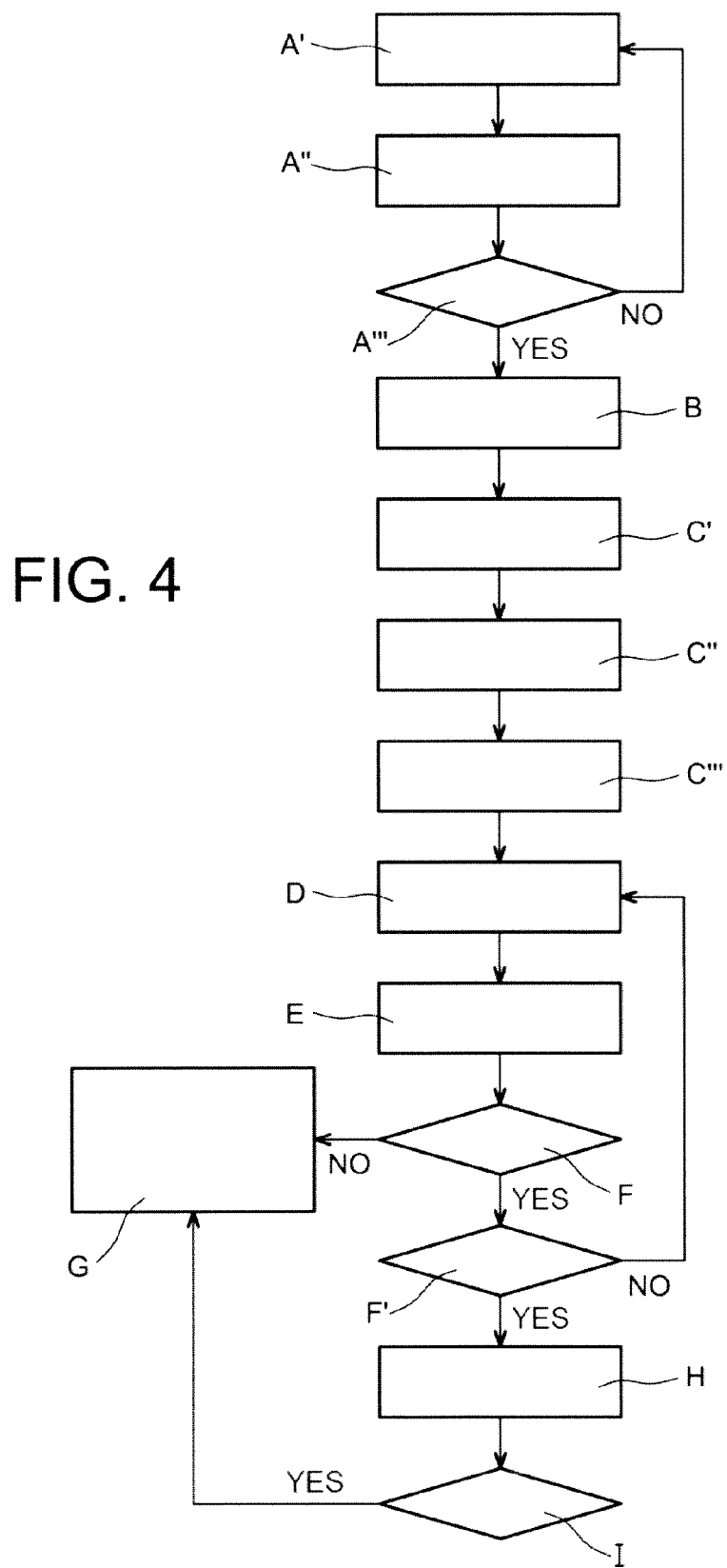
FIG. 4 is a complete flow chart explaining the various steps for implementing a method for detecting anomalies during the filling of a liquid metering device with a liquid to be measured out.

In this way, in this embodiment, as illustrated by the flow chart contained in FIG. 4, step A) comprises the sub-steps A'), A" and A''') consisting of:

A') recording the pressure values measured using the pressure sensor 38 during the filling of the suction cone 10 with a reference volume of liquid, in order to define a pressure variation curve for this reference volume, A") determining the characteristic values $P_{max}$, $t_{max}$, $P_a$, $\tau$ and S corresponding to the pressure variation curve, i.e. the reference curve, obtained for the reference volume, A''') checking whether the pipette 2 is calibrated with all the reference volumes.

In this embodiment, step C) for calculating the tolerance range comprising sub-steps consisting of:

C') calculating the various characteristic values $P_{max}$, $t_{max}$, $P_a$, $\tau$ at the desired volume, C") calculating the calculated filling curve $P_{ref}(t)$ on the basis of these calculated values at the desired volume and the pressure curve for the volume corresponding to the nominal capacity of the pipette 2, and C''') calculating the upper and lower limit of the tolerance range on the basis of the calculated filling curve $P_{ref}(t)$.

Step C') is performed, as described above, on the basis of the characteristic volumes at the reference volume, these characteristic values having been calculated, during step A"), on the basis of the filling curve at the corresponding reference volume, and equations (2), (3), (4), (5) and (6).

The filling is calculated, during step C"), in two stages. The first phase, between 0 and $t_{max}$, includes, as illustrated in FIG. 2, the pressure increasing curve portion corresponding to the nominal capacity of the pipette 2 between these two stages. The second phase, between $t_{max}$ and a time greater than $\tau$, is calculated on the basis of equation (1)

The upper $P_+(t)$ and lower $P_-(t)$ of the tolerance range are calculated, during step C''') using the following equations:

$$P_+(t) = P_{ref}(t) + \Delta P + \left| \frac{P_{mes}(t) - P_{mes}(t - dt)}{dt} \right| \times \Delta t \quad (7)$$

-continued $$P_-(t) = P_{ref}(t) - \Delta P - \left|\frac{P_{mes}(t) - P_{mes}(t-dt)}{dt}\right| \times \Delta t \qquad (8)$$

where ΔP and Δt are the tolerance deviations observed by the manufacturer and dt is the time interval between two pressure measurements.

According to one option of the invention, the upper $P_+(t)$ and lower $P_-(t)$ limits may also be calculated on the basis of the calculated pressure. In this embodiment, such an option may be obtained using the following equations:

$$P_+(t) = P_{ref}(t) + \Delta P + \left|\frac{P_{ref}(t) - P_{ref}(t-dt)}{dt}\right| \times \Delta t$$

$$P_-(t) = P_{ref}(t) - \Delta P - \left|\frac{P_{ref}(t) - P_{ref}(t-dt)}{dt}\right| \times \Delta t$$

In this way, the implementation of the pipette 2 by a user during the metering of any volume of liquid to be measured out consists of performing a prior pressure calibration step of the pipette 2 with a number of reference volumes at least equal to two and comprising, preferably, the volume corresponding to the nominal capacity of the pipette 2. This pressure calibration step may be performed with the liquid to be measured out or a reference liquid, preferentially having the same viscosity as the liquid to be measured out. The pipette 2 is then used in a conventional manner for an automated pipette, i.e. the user performs steps consisting of:
  setting the pipette 2 with the volume of liquid to be measured out,
  placing the suction cone 10 in contact with the liquid to be measured out,
  actuating the pipette 2 such that the processing system 16 controls the filling means for filling the suction cone 10 and implementing the method for detecting anomalies,
  checking whether a warning is displayed on the screen 12 reporting that an anomaly occurred during pipetting.

Figure 5:
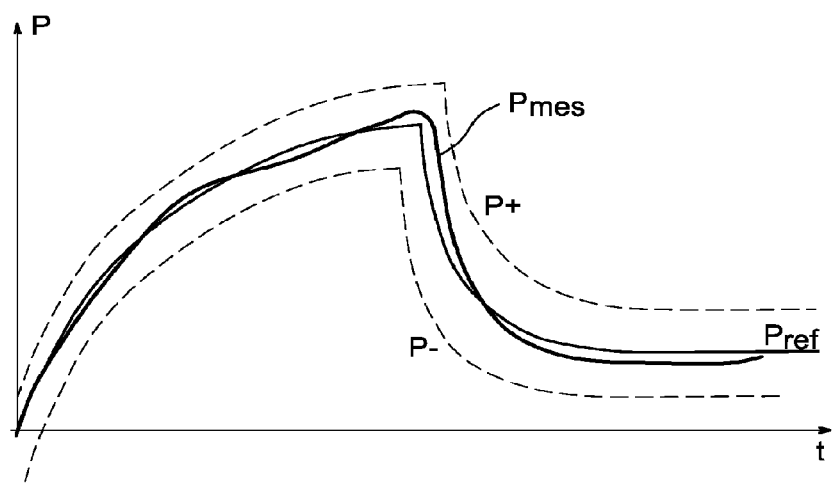
FIG. 5 illustrates an example of a pressure variation curve for successful filling obtained on implementing a method for detecting anomalies during the filling of a device according to the invention.
Figure 6:
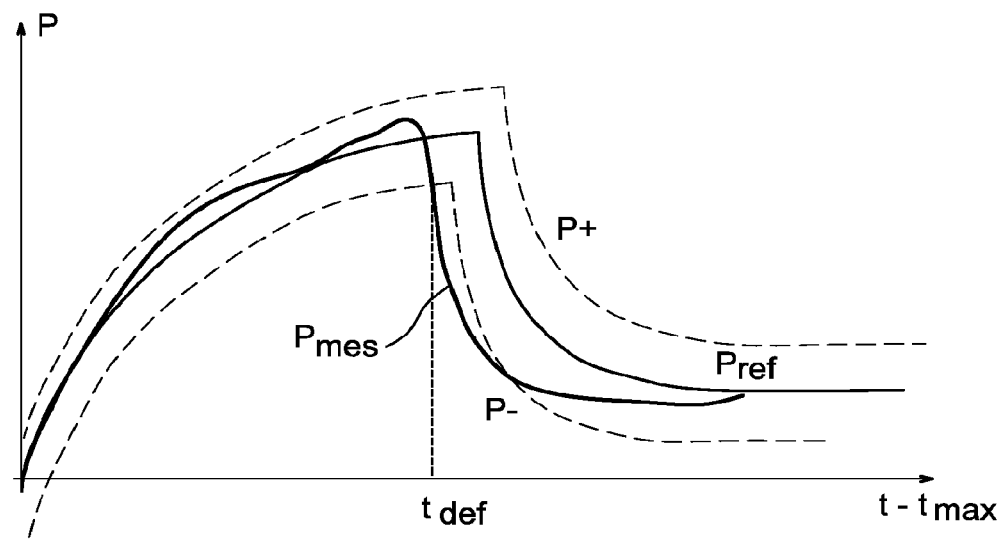
FIG. 6 illustrates an example of a pressure variation curve for filling having an anomaly obtained on implementing a method for detecting anomalies during the filling of a device according to the invention.

FIGS. 5 and 6 are examples of filling curves liable to be obtained during such an implementation of the pipette 2 according to this embodiment. Both these figures show a calculated filling curve $P_{ref}$, the upper $P_+$ and lower limit $P_-$ of the tolerance range corresponding to the calculated filling curve and a measured filling curve $P_{mes}$ showing, respectively, for FIGS. 5 and 6, successful and defective filling.

In this way, it can be seen in FIG. 5 that, during filling, the pressure, according to the filling curve, remains at all times between the upper limit and the lower limit of the tolerance range. No anomaly is thus detected.

Whereas, in FIG. 6, during the filling illustrated, the pressure $P_{mes}$, at the time $t_{def}$, is no longer within the tolerance range. The processing system 16 thus detects an anomaly and shows the user that the filling is defective. The processing system 16, according to the configuration thereof may, either stop, as illustrated in FIG. 6, the actuation of the plunger 30 and thus the filling, or continue same.

Figure 7:
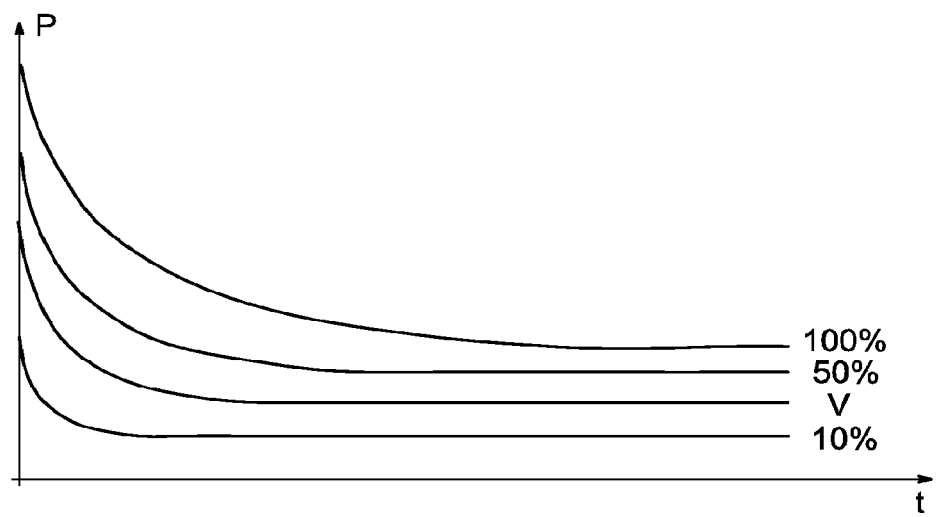
FIG. 7 illustrates filling curves wherein the time variable is a time variable corrected by the value $t_{max}$.

According to a second embodiment of the invention, the filling curve may be the pressure curve, as illustrated in FIG. 7, after the end of the actuation of the plunger 30, i.e. after reaching the time $t_{max}$, the time variable being thus $t-t_{max}$.

Figure 8:
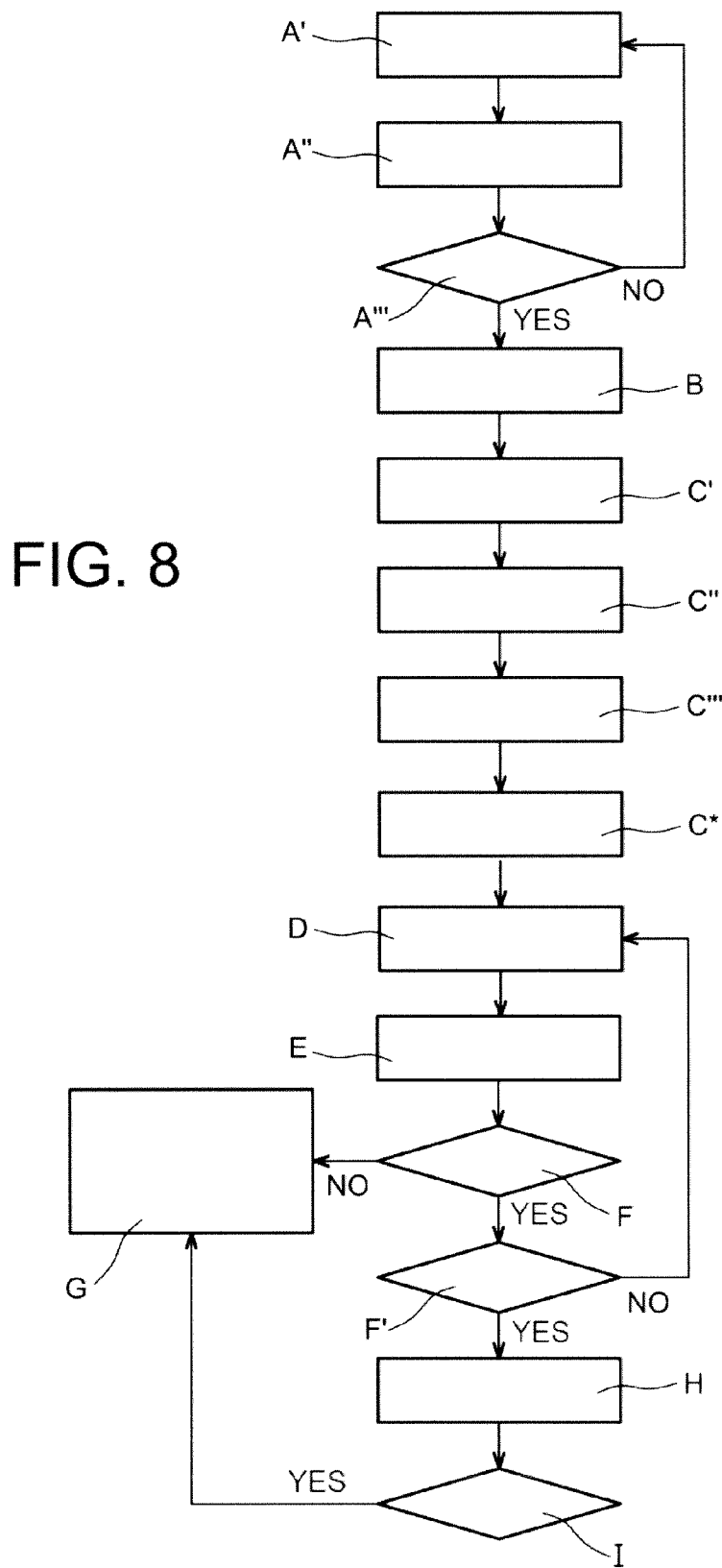
FIG. 8 is a complete flow chart explaining the various steps for implementing a method for detecting anomalies according to one option of the invention wherein the method comprises a step c*) consisting of actuating the filling means for the time $t_{max}$ calculated for the desired volume.

A method according to such an embodiment differs from a method according to the first embodiment in that it comprises, as shown in the flow chart in FIG. 8, a step C*) between step C''') and step D) during which the plunger 30 is actuated, in that step A'') for determining the characteristic values consists of at least calculating the characteristic values $t_{max}$, S and the filling curve at the reference volume, and in that the calculation of the filling curve, performed in step C''), is obtained by means of a linear extrapolation on the basis of two reference filling curves.

In this way, in this embodiment, each filing curve, as illustrated in FIG. 7, is a pressure variation curve after $t_{max}$ showing, when there are no anomalies, a variation according to equation (1).

In this embodiment, step A'') consists of determining for the reference volume at least the characteristic values $t_{max}$ and S and recording the pressure variation $P(t-t_{max})$ during the second phase, i.e. after the end of the actuation of the plunger 30.

In this step, the pressure variation curve $P(t-t_{max})$ during the second phase is the filling curve at the corresponding reference volume.

In step C''), the reference curve may be calculated using a linear extrapolation on the basis of a formula of the following type:

$$P_{ref}(t - t_{max}) = \qquad (9)$$
$$\frac{V - V_1}{V_2 - V_1}(P_{V2}(t - t_{max\_V2}) - P_{V1}(t - t_{max\_V1})) + P_{V1}(t - t_{max\_V1})$$

where $P_{ref}$ is the pressure defining the calculated filling curve for the desired volume, $t_{max}$ is the characteristic value calculated using equation (3), $P_{V2}$ is the pressure defining the filling curve of the reference volume $V_2$, $t_{max\_V2}$ is the characteristic value $t_{max}$ of the reference volume $V_2$, $P_{V1}$ is the pressure defining the filling curve of the reference volume $V_1$ and $t_{max\_V1}$ is the characteristic value $t_{max}$ of the reference volume $V_1$.

This calculation, as illustrated in FIG. 7, enables an approximate determination of the filling curve for the desired volume without requiring the calculation of the characteristic variables at the desired volume other than $t_{max}$.

The upper and lower limits of the tolerance range are calculated in step C''') on the basis of the filling curve calculated during step C'') using equations (7), (8) with the time variable $t-t_{max}$.

During the step C*), the plunger 30 is actuated for the time $t_{max}$ corresponding to the desired volume calculated in step C'') for reaching the pressure $P_{max}$ in the suction chamber 22 and thus filling the suction cone 10, after relaxation of the pressure, with the desired volume of liquid to be measured out.

Step F) for checking that the pressure is present in the tolerance range and thus observes a substantially identical variation to the calculated reference curve is performed after step C*), i.e. at the end of the actuation of the plunger 30 and with a change of time origin and thus a change of time variable, said variable being $t-t_{max}$ in this embodiment.

In use, the implementation of a pipette 2 according to this embodiment remains, for the user, similar to that of pipette 2 according to the first embodiment.

Figure 9:
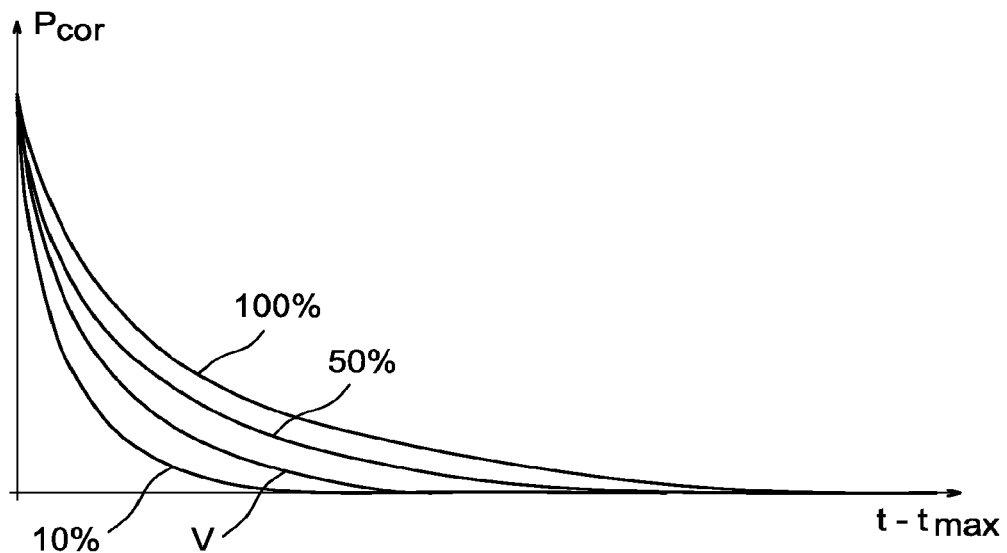
FIG. 9 illustrates filling curves for the corrected factor $P_{cor}$ after the time $t_{max}$.

According to a third embodiment, each of the filling curves may be a pressure curve $P_{cor}$ as illustrated in FIG. 9, after actuating the plunger 30, i.e. after the time $t_{max}$ has been reached, the time variable thus being $t-t_{max}$.

Such a pressure $P_{cor}$ is a pressure obtained with the following equation:

$$P_{cor}(t) = \frac{P_{mes}(t) - P_a}{P_{max} - P_a} \quad (10)$$

In this way, a method according to this embodiment differs from a method according to the second embodiment in that the reference filling curves are pressure curves $P_{cor}$ wherein the time variable $t-t_{max}$ where $t_{max}$ corresponds to the reference volume and in that step A") for determining the characteristic values consists of at least calculating the characteristic values $t_{max}$, $P_a$ and S.

In this embodiment of step C"), the calculated filling curve is calculated according to a similar linear extrapolation calculation to that in equation (9) where the pressure, regardless of whether they are reference or calculated, corresponding to a $P_{cor}$ according to equation (10). The following equation is thus obtained:

$$P_{ref\_cor}(t - t_{max}) = $$
$$\frac{V - V_1}{V_2 - V_1}(P_{V2\_cor}(t - t_{max\_V2}) - P_{V1\_cor}(t - t_{max\_V1})) + P_{V1\_cor}(t - t_{max\_V1})$$

where $P_{ref\_cor}$ is the calculated corrected pressure, $P_{V1\_cor}$ the corrected pressure at the reference volume $V_1$, $P_{V2\_cor}$ the corrected pressure at the reference volume $V_2$ and $t_{max\_V1}$ and $t_{max\_V2}$ the characteristic values $t_{max}$ corresponding to $V_1$ and $V_2$, respectively.

Similarly, during step c''') for calculating the limits of the tolerance range, these limits are calculated according to equations (7) and (8) with $P_{ref\_cor}(t-t_{max})$ and $P_{mes\_cor}(t-tmax)$ instead of $P_{ref}(t)$ and $P_{mes}(t)$, respectively.

In use, the implementation remains, for the user, similar to that of the first embodiment.

Figure 10:
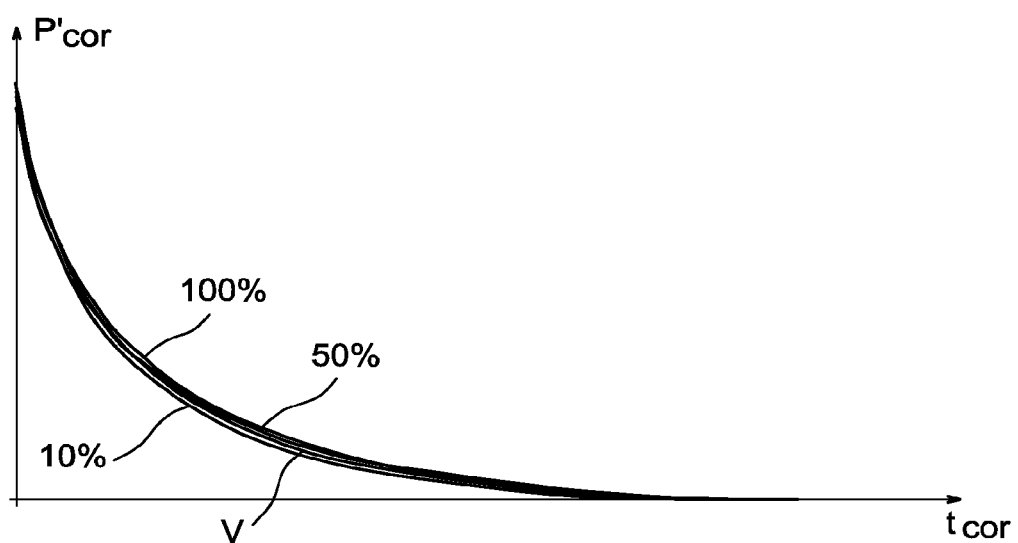
FIG. 10 illustrates filling curves for the corrected factor $P'_{cor}$ as a function of the time variable $t_{cor}$.

According to a fourth embodiment of the method, each of the filling curves may be a pressure curve $P'_{cor}$, as illustrated in FIG. 10, after actuation of the plunger 30 and with a time variable $t_{cor}$.

Such a pressure $P'_{cor}$ is a pressure obtained with the following equation:

$$P'_{cor}(t_{cor}) = \frac{P_{mes}(t_{cor}) - P_a}{P_{max} - P_a}$$
where
$$t_{cor} = \frac{t - t_{max}}{\sqrt{P_{max} - P_a}}.$$

A method according to this embodiment differs from a method according to the third embodiment in that the reference filling curves are pressure curves $P'_{cor}$ wherein the time variable is $t_{cor}$ with characteristic values corresponding to the reference volume and in that step A") for determining the characteristic values consists of at least calculating the characteristic values $t_{max}$, $P_a$, $P_{max}$ and S.

In this embodiment, as illustrated in FIG. 10, all the filling curves have a similar decline. In this way, according to an identical principle to that used in the fourth embodiment, and with increased precision, during step C"), the calculated filling curve is calculated on the basis of a linear extrapolation of the same type as that in equation (9). The equation used is as follows:

$$P'_{ref\_cor}(t_{cor}) = \frac{V - V_1}{V_2 - V_1}(P'_{V2\_cor}(t_{cor}) - P'_{V1\_cor}(t_{cor})) + P'_{V1\_cor}(t_{cor})$$

where $P'_{cal\_cor}$ is the calculated corrected pressure, $P'_{V1\_cor}$ the corrected pressure at the reference volume $V_1$ and $P'_{V2\_cor}$ the corrected volume at the reference volume $V_2$, the relationships at $t_{cor}$ of $P'_{V1\_cor}$ and $P'_{V2\_cor}$ being calculated on the basis of the characteristic values at the corresponding volume, i.e. for example $$P'_{V2\_cor}(t_{cor}) = P'_{V2\_cor}\left(\frac{t - t_{max\_V2}}{\sqrt{P_{max\_V2} - P_{a\_V2}}}\right).$$

Similarly, during step c''') for calculating the limits of the tolerance range, these limits are calculated according to equations (7) and (8) with $P'_{ref\_cor}(t-t_{max})$ and $P'_{mes\_cor}(t-t_{max})$ instead of $P_{ref}(t)$ et $P_{mes}(t)$, respectively.

In use, the implementation of a pipette 2 according to this embodiment remains, for the user, similar to that of a pipette 2 according to the first embodiment.

According to a fifth embodiment, each of the filling curves may be a pressure curve $P''_{cor}$, as illustrated in FIG. 10, after actuating the plunger 30 and with a time variable $t_{cor}$ identical to that used in the fourth embodiment.

Such a pressure $P''_{cor}$ is a pressure obtained using the following equation:

$$P''_{cor}(t_{cor}) = \sqrt{\frac{P_{mes}(t_{cor}) - P_a}{P_{max} - P_a}}$$
where
$$t_{cor} = \frac{t - t_{max}}{\sqrt{P_{max} - P_a}}.$$

A method according to this embodiment differs from a method according to the third embodiment in that the reference filling curves are pressure curves $P''_{cor}$ wherein the time variable is $t_{cor}$ determined on the basis of the characteristic values corresponding to the reference volume.

Figure 11:
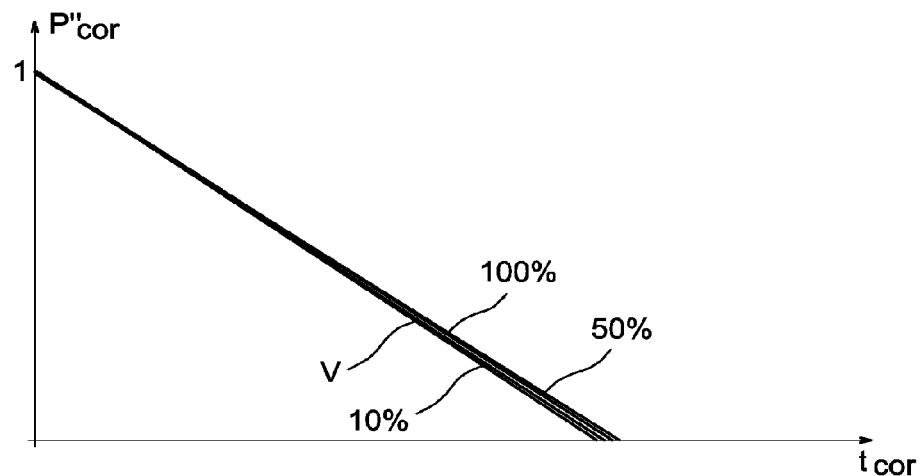
FIG. 11 illustrates filling curves for the corrected factor $P''_{cor}$ as a function of the time variable $t_{cor}$.

In this embodiment, as illustrated by FIG. 11, all the filling curves have a substantially similar decline. In this way, according to an identical principle to that used in the third and fourth embodiments, and with increased precision, during step C"), the calculated filling curve is calculated on the basis of a linear extrapolation of the same type as that in equation (9). The equation used is thus as follows:

$$P''_{ref\_cor}(t_{cor}) = \frac{V - V_1}{V_2 - V_1}(P''_{V2\_cor}(t_{cor}) - P''_{V1\_cor}(t_{cor})) + P''_{V1\_cor}(t_{cor})$$

where $P''_{ref\_cor}$ is the calculated corrected pressure, $P''_{V1\_cor}$ the corrected pressure at the reference volume $V_1$ and $P''_{V2\_cor}$ the corrected pressure as the reference volume $V_2$.

As for the fourth embodiment, the relationships at $t_{cor}$ of $P''_{V2\_cor}$ and $P''_{V2\_cor}$ in this equation are calculated on the basis of the characteristic values at the corresponding volume, i.e. for example $$P''_{V2\_cor}(t_{cor}) = P''_{V2\_cor}\left(\frac{t - t_{max\_V2}}{\sqrt{P_{max\_V2} - P_{a\_V2}}}\right).$$

In use, the implementation of a pipette 2 according to this embodiment remains, for the user, similar to that of a pipette 2 according to the first embodiment.

According to one option of the invention, the processing system 16 may also be suitable for detecting anomalies during the release of the liquid contained in the suction cone 10.

Such suitability may be carried out in a similar manner to the suitability for detecting anomalies during filling.

Figure 12:
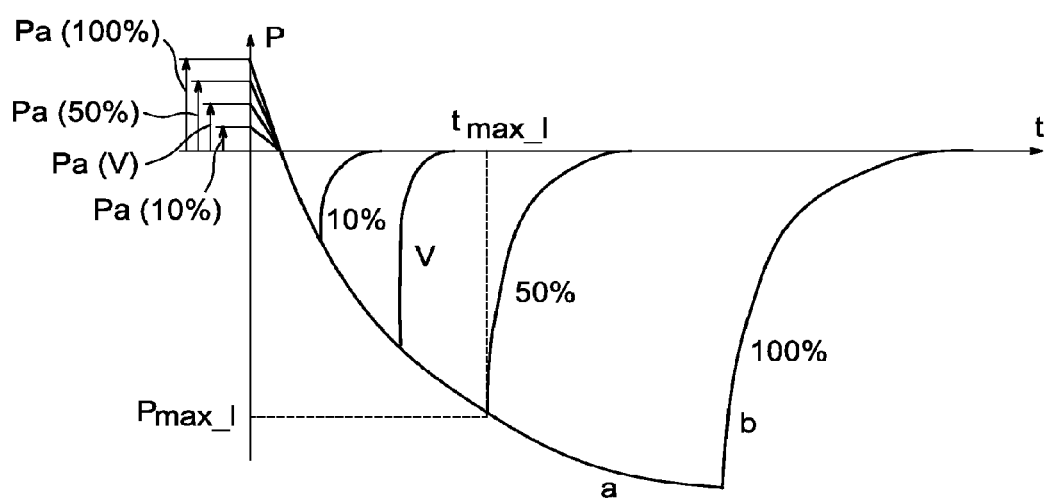
FIG. 12 illustrates curves for the release of a liquid to be measured out by a metering device for various liquid volumes.

Indeed, FIG. 12 illustrates so-called release pressure curves, which may be recorded using the pressure sensor 38 on the release of the liquid contained in the suction cone.

These pressure curves have, similar to the pressure curves recorded during filling, two phases, a reversal and subsequently pressure rise phase a') and a phase for returning the pressure to the atmospheric pressure value.

At the start of the first phase, the pressure measured by the pressure sensor corresponds to the residual vacuum pressure $P_a$ remaining after the filling of the pipette 2. The actuation of the plunger to release the liquid gives rise to a gradual decrease in the vacuum pressure with a transition to atmospheric pressure followed by an overpressure phase. During this phase, after the pressure has reached atmospheric pressure, the pressure variation is substantially identical regardless of the quantity of liquid contained in the pipette 2 and in the pressure reaches a pressure value $P_{max\_l}$ at a time $t_{max\_l}$. $P_{max\_l}$ and $t_{max\_l}$ are characteristic values of the release curve at a given liquid volume.

The second phase corresponds, after stopping the actuation of the plunger to release the liquid, to the return to atmospheric pressure. This second phase observes a pressure variation which can be modelled using the following equation:

$$P(t) = P_{max\_l} \times \left(1 - \frac{t - t_{max\_l}}{\tau_l}\right)^2$$

where $\tau l$ is a characteristic value suitable for being calculated at any time t of the phase for returning to atmospheric pressure using the following equation:

$$\tau l = \frac{t - t_{max\_l}}{1 - \sqrt{\frac{p(t)}{P_{max\_l}}}}$$

As for the filling phase, it is possible to determine with sufficient precision the characteristic values corresponding to the release phase for a given volume by performing a linear extrapolation on the basis of reference pressure curves. In this way, according to the example of the curves shown in FIG. 12, it is possible to determine the characteristic values for the volume V with the reference curves encompassing same, i.e. for the curves corresponding to 10% and 50% of the nominal capacity of the pipette 2.

Those skilled in the art, having knowledge of the method for detecting anomalies during the filling of the pipette described above, can readily apply similar reasoning to that described for said method, the calculations enabling this extrapolation are thus not described for the method for detecting anomalies during the release of the liquid to be measured out.

On the basis of the pressure curves in FIG. 12, it is also possible to determine the characteristic value $S_l$ which is characteristic of the ratio between the volume of liquid contained in the suction cone 10 prior to release and the integral of the pressure variation during said release.

This characteristic value may be calculated using the following equation:

$$S_l(V) = \frac{\sqrt{\frac{\rho}{2}} V}{\int_0^{t_{max\_l}} \sqrt{P_a - P(t)}\, dt + \int_{t_{max\_l}}^{t_{max\_l}+\tau l} \sqrt{-P(t)}\, dt}$$

where ρ is the viscosity of the liquid.

This parameter may thus be suitable, for a given volume of liquid to be measured out, for checking whether the pressure variation during the release of the liquid by the pipette 2 is consistent with the given volume contained therein, and thus for checking whether the released volume of liquid to be measured out is indeed that expected.

Indeed, according to the above equation, the volume of liquid released is equal to:

$$V_{cal} = S \sqrt{\frac{\rho}{2}} \left( \int_0^{t_{max\_l}} \sqrt{P_a - P(t)}\, dt + \int_{t_{max\_l}}^{t_{max\_l}+\tau l} \sqrt{-P(t)}\, dt \right)$$

This volume $V_{cal}$ may readily be compared to the volume of liquid to be measured out theoretically contained in the suction cone 10.

In this way, all or some of the characteristic values of the release of liquid by the pipette, $P_{min}$, $t_{min}$, $P_a$, $\tau l$ and $S_l$ may be calculated for any volume of liquid to be measured out and thus be used for detecting an anomaly during the release by the pipette of said volume of liquid to be measured out.

The processing system 16 of the pipette 2 is suitable for implementing this principle during the implementation of a method for detecting anomalies during the release of a liquid to be measured out.

Figure 13:
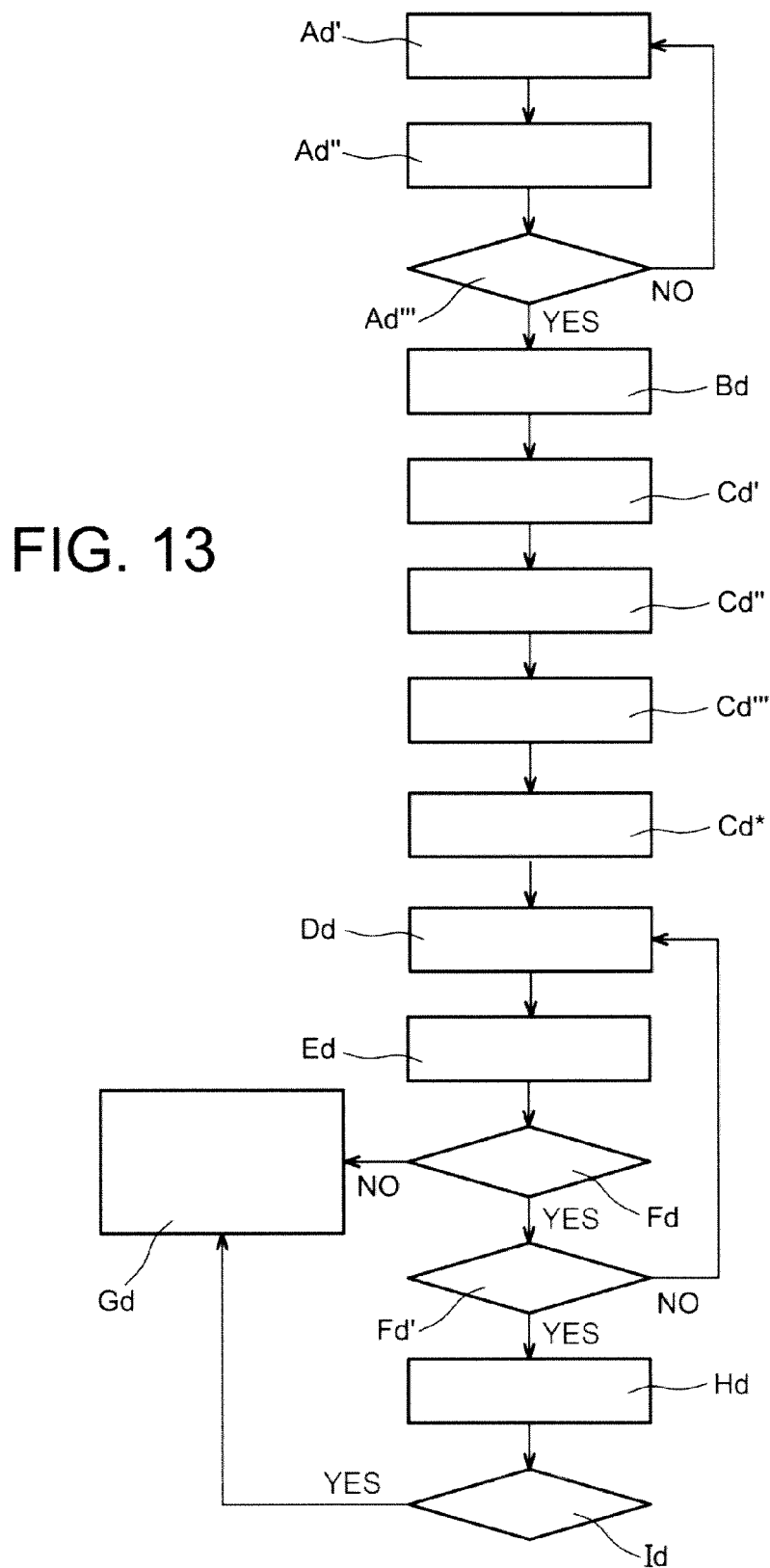
FIG. 13 is a complete flow chart explaining the various steps for implementing a method for detecting anomalies on releasing the liquid to be measured out.

FIG. 13 is a flow chart showing the steps of such a method. Such a method comprises steps consisting of:

Ad') recording the pressure values measured using the pressure monitoring means during the release of a reference volume of liquid contained in the suction cone 10, Ad'') determining the characteristic values corresponding to the pressure curve obtained for the reference volume, Ad''') checking that the pipette 2 is calibrated with all the reference volumes, Bd) defining a desired volume of liquid to be measured out, Cd') calculating a calculated release curve for the desired volume on the basis of the reference filling curves, Cd'') performing a step for calculating the upper and lower limits of a release tolerance range by respectively subtracting and adding a pressure value ΔP to the calculated release curve.

Cd''') performing a step for calculating the upper and lower limits of the release tolerance range by respectively creating a positive and negative time lag by a time value Δt of the upper and lower limits calculated during step Cd''), Cd*) actuating the plunger 30 during the time $t_{max\_1}$ corresponding to the desired volume calculated in step Cd") suitable for reaching the pressure $P_{max\_1}$ in the suction chamber 22 and thus for draining the suction cone 10, after relaxation of the pressure in the suction chamber 22, Dd) releasing a portion of the liquid to be measured out from the suction cone 10 for a time dt, Ed) measuring the pressure using the pressure sensor 28, Fd) checking whether the pressure is within the tolerance range, Fd') checking whether t is greater than or equal to the release time corresponding to the desired volume, Gd) reporting that an anomaly has been detected, Hd) calculating the volume of liquid to be measured out released, Id) checking whether the difference between the calculated volume of liquid to be measured out and the desired volume is greater in absolute terms than a threshold value.

Similarly to the various embodiments described above in relation to the method for detecting anomalies during the filling of the pipette 2, those skilled in the art can adapt, in a similar manner, the processing system 16 for the implementation of various embodiments of the method for detecting anomalies on the release of the liquid to be measured out.

In this way, the release curve may be a pressure curve after $t_{max\_1}$, a corrected pressure curve of a similar type to $P_{cor}(t-t_{max})$, or a corrected pressure curve of a similar type to $P'_{cor}(t_{cor})$ or $P'_{cor}(t_{cor})$ with a time variable of a similar type to $t_{cor}$, without leaving the scope of the invention.

According to two options of the invention, the pressure calibration steps in step A) and those in step Ad) may be carried out during the manufacture of the pipette to provide a ready-to-use pipette 2 or performed prior to the use of the pipette 2 so that the user can adapt the processing system to detect an anomaly during filling and/or during the release of the liquid to be measured out. These two options are mutually compatible, the user having the option of using standard pressure calibration for quick measurements not requiring high precision and the option of pressure calibration suitable for a liquid to be measured out having a particular viscosity and/or for measurements requiring anomaly detection which is refined and/or compatible with particular experimental conditions (particular filling and/or release rates, definition of suitable reference volumes, etc.)

Similarly, the values ΔP and Δt, used for calculating the tolerance range, may be set in the factory, during the production of the pipette 2, or entered by the user before the first use. These two options are compatible, the user having, in this case, the choice of operating with a standard tolerance range or with a tolerance range adapted to requirements.

According to one option of the invention, the processing system may also be suitable for identifying the cause of the filling or release anomaly and reporting same to the user if the pipette 2 is equipped with a screen 12.

In this way, during filling if the filling curve exhibits combined low values of $t_{max}$, $P_{max}$ and the calculated volume, it may be identified that the stroke of the plunger 30 is too short, the processing system 16 optionally, in this case, compensating by actuating the plunger 30 so as to compensate for the low values.

If a high $t_{max}$ is measured in conjunction with a low $P_{max}$, the processing system may report that the speed of the plunger 30 is too low, the processing system optionally, in this case, compensating by increasing the speed of the plunger 30.

Similarly, if the pressure signal remains substantially equal to atmospheric pressure during the filling of the pipette 2, the processing system may report that the suction cone 10 is not immersed in the liquid.

If the pressure signal has no relaxation phase b), the processing system may report that the suction cone 10 is blocked and thus needs to be replaced.

If $t_{max}$ exhibits an expected value and $P_{max}$ and the calculated volume $V_{cal}$ both exhibit a low value, the processing system may report a leak between the plunger 30 and the suction chamber 22 and that the pipette 2 needs to be serviced.

According to a further option of the invention, the processing system may be suitable for enabling recording of the successive pressure curves so as to enable traceability of the measurements made using the pipette 2. This option is particularly useful for an automated pipetting system, such as that of an automated chemical analyser.

Similarly, while all the embodiments described above relate to an automated pipette 2, the invention is not limited merely to automated pipettes 2 having a single suction cone 10 but relates to all metering devices having an automated filling system, such as for example automated chemical analysers or double pipettes, having a dual suction system comprising two suction chambers 22, two suction cones 10 and two plungers 30, or multiple suction systems comprising more than two suction chambers 22, compatible with a plurality of suction cones 10 and comprising a plurality of plungers 30.

It should also be noted that while, in this embodiment of the pipette 2 described above, the pressure sensor 38 acting as the pressure monitoring means is the pressure sensor 38 present in the suction chamber 22, the pressure sensor 38 may also be arranged so as to measure the pressure in the suction cone 10. Indeed, the pressure variation curves obtained using a pressure sensor 38 present in the suction chamber 22 and using a pressure sensor 38 suitable for measuring the pressure in the suction cone 10 exhibit a substantially identical variation.

While, in all the embodiments described above, the warning means consist of a screen, it can also be envisaged, without leaving the scope of the invention, that the pipette comprises, substituting or in addition to the screen, an audio alarm signalling to the user the existence of an anomaly during the filling of the pipette. According to this option, if the warning means consist solely of the audio alarm, the sound from this alarm may be modulated to report the type of anomaly to the user.

The invention claimed is:

1. A method for detecting anomalies during the filling of a liquid metering device with a liquid to be measured out, said metering device comprising:
   at least one suction member adapted to be in contact with the liquid to be measured out and to contain same during the filling of the metering device,
   at least one filling means arranged for filling, in an automated manner, the suction member, said filling means comprising at least one zone communicating with the suction member, said zone containing a gas,
   and at least one pressure monitoring means arranged for measuring the pressure in the at least one zone of the filling means or in a zone of the suction member containing a gas,
   the detection method comprising steps consisting of:
   a) performing a prior pressure calibration of the filling of the metering device, said pressure calibration being carried out with at least two reference volumes so as to define a reference filling curve for each of the at least two reference volumes and to determine for each reference volume
- a maximum vacuum pressure value $P_{max\_V1}$, $P_{max\_V2}$ corresponding to a maximum vacuum pressure value reached during filling;
- a maximum vacuum pressure time $t_{max\_V1}$, $t_{max\_V2}$ corresponding to a time at which the maximum vacuum pressure value is reached;
- a residual vacuum pressure $P_{a\_V1}$, $P_{a\_V2}$ corresponding to a residual vacuum pressure after filling the metering device; and
- a characteristic time $\tau_{\_v1}$, $\tau_{13\ v2}$ representing a rate of decline of the vacuum pressure after the vacuum pressure value $P_{max\_V1}$, $P_{max\_V2}$ has been reached;

b) defining a desired volume of liquid to be measured out;

c) calculating for the desired volume a tolerance range having an upper limit and a lower limit, the upper and lower limits of the tolerance range being calculated on the basis of the reference filling curves a calculated filling curve using the following equation $$P_{ref}(t) = [P_{max} - P_a] \times \left(1 - \frac{t - t_{max}}{\tau}\right)^2 + P_a,$$

wherein $P_{max}$ is interpolated from $P_{max\_V1}$, $P_{max\_V2}$, Pa is interpolated from $P_{a\_V1}$, $P_{a\_V2}$, $t_{max}$ is interpolated from $t_{max\_V1}$, $t_{max\_V2}$, and wherein $\tau$ is calculated using the following equation $$\tau = \frac{\sqrt{P_{max} - P_a}}{V_2 - V_1} \left( \frac{\tau_{V2}(V - V_1)}{\sqrt{P_{max\_V2} - P_{a\_V2}}} - \frac{\tau_{V1}(V - V_2)}{\sqrt{P_{max\_V1} - P_{a\_V1}}} \right);$$

d) filling the suction member with the liquid to be measured out for a time dt;

e) measuring the pressure using the pressure monitoring means;

f) checking whether the pressure is within the tolerance range and if the pressure is in the tolerance range returning to step d) until a filling time corresponding to the desired volume of liquid to be measured out is attained; and g) if the pressure is outside the tolerance range, reporting that an anomaly has been detected.

2. The method according to claim 1, further comprising;
- a step h) consisting of calculating, on the basis of the pressures measured during the filling of the metering device, the volume of liquid to be measured out in the suction member; and
- a step i) consisting of, if the difference between the desired volume and the calculated volume of liquid to be measured out is greater, in absolute terms, than a threshold value, reporting that an anomaly has been detected.

3. The method according to claim 1, wherein step c) further comprises:
- a step c') consisting of calculating a filling curve calculated for the desired volume on the basis of the reference filling curves; and
- a step c'') during which the calculation of the upper and lower limits of the tolerance range comprises a calculation step for the upper limit and the lower limit of respectively adding and subtracting a pressure value $\Delta P$ to the calculated filling curve.

4. The method according to claim 1, wherein step c) further comprises:
- a step c') consisting of calculating a filling curve calculated for the given volume on the basis of the reference filling curves; and
- a step c''') during which the calculation of the upper and lower limits of the tolerance range comprises a calculation step consisting, for the upper limit and the lower limit, of respectively creating a positive and negative time lag by a time value $\Delta t$.

5. The method according to claim 1, wherein step a) further comprises:
- a step a') consisting of recording pressure values measured using the pressure monitoring means during the filling of the suction member with a reference volume of liquid; and
- a step a'') consisting of determining the filling curve corresponding to the pressure curve obtained in step a'), said step a'') also optionally consisting of determining the characteristic values corresponding to said pressure curve, steps a') and a'') being carried out for each of the reference volumes.

6. The method according to claim 1, wherein step c) further comprises;
- a step c') consisting of calculating a filling curve calculated for the desired volume on the basis of the reference filling curves; and
- a step c'') during which the calculation of the upper and lower limits of the tolerance range comprises a calculation step for the upper limit and the lower limit of respectively subtracting and adding a pressure value $\Delta P$ to the calculated filling curve, and
- wherein step c') further comprises step consisting of linearly interpolating the filling curve and/or characteristic values of the filling curve at the desired volume on the basis of at least two reference volume filling curves and/or characteristic values of the pressure curves of at least two reference volumes.

7. The method according to claim 6, wherein step c) further comprises:
- a step c') consisting of calculating a filling curve calculated for the given volume on the basis of the reference filling curves; and
- a step c''') during which the calculation of the upper and lower limits of the tolerance range comprises a calculation step consisting, for the upper limit and the lower limit, of respectively creating a positive and negative time lag by a time value $\Delta t$, and
- wherein, during steps c'') and c'''), the upper and lower limits of the tolerance range are calculated on the basis of the calculated filling curve at step c') using the following formulae:

$$P_+(t) = P_{ref}(t) + \Delta P + \left|\frac{dP(t)}{dt}\right| \times \Delta t,$$

$$P_-(t) = P_{ref}(t) - \Delta P - \left|\frac{dP(t)}{dt}\right| \times \Delta t,$$

where $P_+(t)$ and $P_-(t)$ are the upper and lower limits of the tolerance range at a time t, $P_{ref}(t)$ is the pressure calculated at the time t on the basis of the calculated filling curve and P(t) is the pressure variation measured at the time t.

8. The method according to claim 6, wherein the method further comprises, between steps c) and d), a step c*) consisting of operating the filling means for the time $t_{max}$ calculated for the desired volume, and wherein the reference and calculated filling curves are the pressure variation curves after the corresponding time $t_{max}$.

9. The method according to claim 6, wherein the method further comprises, between steps c) and d), a step c*) consisting of operating the filling means for the time $t_{max}$ calculated for the desired volume, and wherein the reference and calculated filling curves are the variation curves of a factor $P_{cor}$ after the time $t_{max}$, the factor $P_{cor}(t)$ being equal to $$\frac{P(t) - P_a}{P_{max} - P_a}.$$

10. The method according to claim 6, wherein the method further comprises, between steps c) and d), a step c*) consisting of operating the filling means for the time $t_{max}$ calculated for the desired volume, and wherein the reference and calculated filling curves are the variation curves of a factor $P'_{cor}$ after the time $t_{max}$ as a function of a time variable $t_{cor}$, the factor $P'_{cor}(t_{cor})$ being equal to $$\frac{P(t_{cor}) - P_a}{P_{max} - P_a}$$

and the time variable $t_{cor}$ being equal to $$\frac{t - t_{max}}{\sqrt{P_{max} - P_a}}.$$

11. The method according to claim 6, wherein the method further comprises, between steps c) and d), a step c*) consisting of operating the filling means for the time $t_{max}$ calculated for the desired volume, and wherein the reference and calculated filling curves are the variation curves of a factor $P'_{cor}$ after the time $t_{max}$ as a function of a time variable $t_{cor}$, the factor $P'_{cor}(t_{cor})$ being ,equal to $$\sqrt{\frac{P(t_{cor}) - P_a}{P_{max} - P_a}}$$

and the time variable $t_{cor}$ being equal to $$\frac{t - t_{max}}{\sqrt{P_{max} - P_a}}.$$

12. The method according to claim 1, wherein step c) further comprises a step c') consisting of calculating a filling curve calculated for the given volume on the basis of the reference filling curves; and a step c''') during which the calculation of the upper and lower limits of the tolerance range comprises a calculation step consisting, for the upper limit and the lower limit, of respectively creating a positive and negative time lag by a time value $\Delta t$, and wherein step c') further comprises a step consisting of linearly interpolating the filling curve and/or characteristic values of the filling curve at the desired volume on the basis of at least two reference volume filling curves and/or characteristic values of the pressure curves of at least two reference volumes.

13. The method according to claim 12, wherein the method further comprises, between steps c) and d), a step c*) consisting of operating the filling means for the time $t_{max}$ calculated for the desired volume, and wherein the reference and calculated filling curves are the pressure variation curves after the corresponding time $t_{max}$.

14. The method according to claim 12, wherein the method further comprises, between steps c) and d), a step c*) consisting of operating the filling means for the time $t_{max}$, calculated for the desired volume, and wherein the reference and calculated filling curves are the variation curves of a factor $P_{cor}$ after the time $t_{max}$, the factor $P_{cor}(t)$ being equal to $$\frac{P(t) - P_a}{P_{max} - P_a}.$$

15. The method according to claim 12, wherein the method further comprises, between steps c) and d), a step c*) consisting of operating the filling means for the time $t_{max}$ calculated for the desired volume, and wherein the reference and calculated filling curves are the variation curves of a factor $P'_{cor}$ after the time $t_{max}$ as a function of a time variable $t_{cor}$, the factor $P'_{cor}(t_{cor})$ being equal to $$\frac{P(t_{cor}) - P_a}{P_{max} - P_a}$$

and the time variable $t_{cor}$ being equal to $$\frac{t - t_{max}}{\sqrt{P_{max} - P_a}}.$$

16. The method according to claim 12, wherein the method further comprises, between steps c) and d), a step c*) consisting of operating the filling means for the time $t_{max}$ calculated for the desired volume, and wherein the reference and calculated filling curves are the variation curves of a factor $P''_{cor}$ after the time $t_{max}$ as a function of a time variable $t_{cor}$ the factor $P''_{cor}(t_{cor})$ being equal to $$\sqrt{\frac{P(t_{cor}) - P_a}{P_{max} - P_a}}$$

and the time variable $t_{cor}$ being equal to $$\frac{t - t_{max}}{\sqrt{P_{max} - P_a}}.$$

17. The method according to claim 1, wherein the method further comprises, between steps c) and d), a step c*) consisting of operating the filling means for the time $t_{max}$ calculated for the desired volume.

18. A liquid metering device suitable for implementing a method according to claim 1, the metering device comprising:
- at least one suction member adapted to be in contact with a liquid to be measured out and to contain same during filling of the metering device;
- at least one filling means arranged for filling, in an automated manner, the suction member, said filling means comprising at least one zone communicating with the suction member, said zone containing a gas;
- at least one pressure monitoring means arranged for recording the pressure in the zone of the filling means or in a zone of the suction member containing a gas;
- warning means suitable for reporting the presence of an anomaly; and
- control and calculating means arranged for controlling the filling means and at least one pressure monitoring means, the control and calculating means being configured for carrying out a pressure calibration of the filling of the metering device with at least two reference volumes and defining a reference curve for each of the at least two reference volumes, and for determining for each of the at least two reference volumes
  - a maximum vacuum pressure value $P_{max\_V1}$, $P_{max\_V2}$ corresponding to a maximum vacuum pressure value reached during filling;
  - a maximum vacuum pressure time $t_{max\_V1}$, $t_{max\_V2}$ corresponding to a time at which the maximum vacuum pressure value is reached;
  - a residual vacuum pressure $P_{a\_V1}$, $P_{a\_V2}$ corresponding to a residual vacuum pressure after filling the metering device; and
  - a characteristic time $\tau_{\_V1}$, $\tau_{\_V2}$ representing a rate of decline of the vacuum pressure after the vacuum pressure value $P_{max\_V1}$, $P_{max\_V2}$ has been reached,
- wherein the control and calculating means is further configured for calculating, for a desired volume of liquid to be measured out, an upper limit and a lower limit of the tolerance range for the desired volume, the upper and lower limits of the tolerance range being calculated by the control and calculating means on the basis of the calculated filling curve using the following equation $$P_{ref}(t) = [P_{max} - P_a] \times \left(1 - \frac{t - t_{max}}{\tau}\right)^2 + P_a,$$

wherein $P_{max}$ is interpolated from $P_{max\_V1}$, $P_{max\_V2}$, Pa is interpolated from $P_{a\_V1}$, $P_{a\_V2}$, $t_{max}$ is interpolated from $t_{max\_V1}$, $t_{max\_V2}$, and wherein $\tau$ is calculated using the following equation $$\tau = \frac{\sqrt{P_{max} - P_a}}{V_2 - V_1}\left(\frac{\tau_{V2}(V - V_1)}{\sqrt{P_{max\_V2} - P_{a\_V2}}} - \frac{\tau_{V1}(V - V_2)}{\sqrt{P_{max\_V1} - P_{a\_V1}}}\right);$$

and for checking whether the pressure remains in said tolerance range during filling, said control and calculating means being further arranged for communicating with the warning means.

19. The liquid metering device according to claim 18, wherein the liquid metering device also implements a method for detecting anomalies on the release of the liquid to be measured out.

20. A method for detecting anomalies during the release of liquid to be measured out by a liquid metering device, said metering device comprising:
- at least one suction member adapted to be in contact with the liquid to be measured out and to contain same during the filling of the metering device,
- at least one filling means arranged for filling, in an automated manner, the suction member, said filling means comprising at least one zone communicating with the suction member, said zone containing a gas,
- and at least one pressure monitoring means arranged for measuring the pressure in the zone of the filling means or in a zone of the suction member containing a gas, the detection method comprising steps consisting of:
Ad) performing a prior pressure calibration of the release of liquid to be measured out by the metering device, said pressure calibration being carried out with at least two reference volumes so as to define a reference releasing curve for each of the at least two reference volumes, and to determine for each reference volume
  a maximum vacuum pressure value $P_{max\_1\_V1}$, $P_{max\_1\_V2}$ corresponding to a minimum vacuum pressure value reached during releasing,
  a maximum vacuum pressure time $t_{max\_1\_V1}$, $t_{max\_1\_V2}$ corresponding to a time at which the minimum vacuum pressure is reached,
  and a characteristic time $\tau_{1\_V1}$, $\tau_{1\_V2}$ representing a rate of decline of the vacuum pressure after the vacuum pressure value $P_{max\_1\_V1}$, $P_{max\_1\_V2}$ has been reached,
Bd) defining a desired volume of liquid to be measured out to be released;
Cd) calculating for the desired volume a tolerance range having an upper limit and a lower limit, the upper and lower limits of the tolerance range being calculated on the basis of a calculated filling curve using the following equation $$P(t) = P_{max\_l} \times \left(1 - \frac{t - t_{max\_l}}{\tau_l}\right)^2,$$

wherein $P_{max\_l}$ is interpolated from $P_{max\_1\_V1}$, $P_{max\_1\_V2}$, $t_{max\_l}$ is interpolated from $t_{max\_1\_V1}$, $t_{max6\_1\_V2}$, and wherein $\tau_l$ is calculated using the following formula $$\tau_l = \frac{\sqrt{P_{max}}}{V_2 - V_1}\left(\frac{\tau_{l\_V2}(V - V_1)}{\sqrt{P_{max\_l\_V2}}} - \frac{\tau_{l\_V1}(V - V_2)}{\sqrt{P_{max\_l\_V1}}}\right);$$

Dd) releasing from the suction member the liquid to be measured out for a time dt;
Ed) measuring the pressure using the pressure monitoring means;
Fd) checking whether the pressure is within the tolerance range and if the pressure is in the tolerance range returning to step Dd) until a releasing time corresponding to the desired released volume of liquid to be measured out is attained; and
Gd) if the pressure is outside the tolerance range, reporting that an anomaly has been detected.

* * * * *